United States Patent [19]

Goodwin

[11] Patent Number: 4,599,827
[45] Date of Patent: Jul. 15, 1986

[54] METALLOGRAPHIC PREPARATION OF PARTICULATE FILLED ALUMINUM METAL MATRIX COMPOSITE MATERIAL

[75] Inventor: Eugene L. Goodwin, Huntsville, Ala.

[73] Assignee: The United States of America as represented by the Secretary of the Army, Washington, D.C.

[21] Appl. No.: 747,741

[22] Filed: Jun. 24, 1985

[51] Int. Cl.⁴ .............................................. B24B 1/00
[52] U.S. Cl. .................................... 51/326; 51/281 R
[58] Field of Search ................ 51/283 R, 284 R, 326, 51/281 R, 135 R, 318, 317

[56] References Cited

U.S. PATENT DOCUMENTS

| | | | |
|---|---|---|---|
| 2,453,709 | 11/1948 | Hughes et al. | 51/281 R |
| 2,554,070 | 5/1951 | Stead | 51/284 |
| 2,802,317 | 8/1957 | Stuck | 51/213 |
| 3,177,627 | 4/1965 | Guibert et al. | 51/135 |
| 3,183,629 | 5/1965 | Ver Meulen | 51/135 R |
| 3,460,295 | 8/1969 | Teeter | 51/283 |
| 3,587,196 | 6/1971 | Dunn | 51/326 |
| 3,662,500 | 5/1972 | Mendel | 51/326 |
| 3,858,369 | 1/1975 | Dolgov et al. | 51/283 |
| 4,406,189 | 9/1983 | Neefe | 51/284 R |

Primary Examiner—Frederick R. Schmidt
Assistant Examiner—Bradley I. Vaught
Attorney, Agent, or Firm—Anthony T. Lane; Robert P. Gibson; James T. Deaton

[57] ABSTRACT

A method of preparing a particulate filled aluminum metal matrix composite material so that it can effectively be examined microscopically and including first rough grinding the sample to produce a flat surface, secondly fine grinding the sample, thirdly rough polishing the sample and fourth and final polishing of the sample to produce a sample with a quality flat and polished surface that can be microscopically examined.

6 Claims, 2 Drawing Figures

METALLOGRAPHIC PREPARATION OF PARTICULATE FILLED ALUMINUM METAL MATRIX COMPOSITE MATERIAL

DEDICATORY CLAUSE

The invention described herein may be manufactured, used, and licensed by or for the Government for governmental purposes without the payment to me of any royalties thereon.

BACKGROUND OF THE INVENTION

In the past, standard metallographic preparation methods have not been acceptable in that their polishing procedures rounded the silicon carbide particles and left them in relief and the aluminum was not scratch-free and clean using these processes. Accordingly, there is a need for a metallographic preparation method for preparation of particulate filled aluminum metal matrix composite material having silicon therein.

Therefore, it is an object of this invention to provide a new preparation method that enables one to obtain a flat, scratch-free, representative sample of a subject aluminum metal matrix composite material for microscopic examination and evaluation.

Another object of this invention is to provide a preparation method in which simple grinding and polishing steps are provided but yet accomplish precision samples for examination and evaluation.

A further object of this invention is to provide a method which brings out the shape and size of the individual particulate in the aluminum metal matrix in the composite material.

Still further object of this invention is to provide a preparation method in which the silicon carbide particles are not left in relief and a process in which the aluminum is left scratch-free and clean.

Other objects and advantages of this invention will be obvious to those skilled in this art.

SUMMARY OF THE INVENTION

In accordance with this invention, a metallographic preparation method is disclosed for the preparation of particulate filled aluminum metal matrix composite material having approximately 25 percent silicon therein. The method includes first cutting the sample to size, mounting the sample in a plastic to provide a holder for the sample, then rough grinding the sample on a belt grinder, next fine grinding the sample on a multiplicity of different grit size silicon carbide paper, rough polishing the sample after fine grinding using a flat aluminum wheel with nylon polishing cloth and diamond bort paste thereon and finally final polishing the sample using a 3-step final polishing procedure to produce a sample of fine quality which is ready for microscopic examination to determine quality and completeness of the polishing method.

DESCRIPTION OF THE PREFERRED EMBODIMENT

Figure 1:
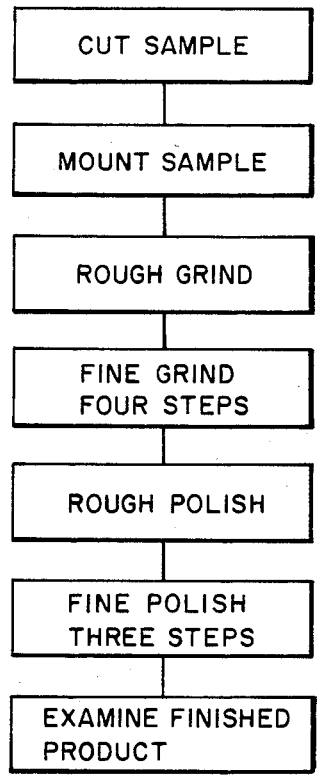
FIG. 1 is a flow diagram illustrating the various steps of the method.
Figure 2:
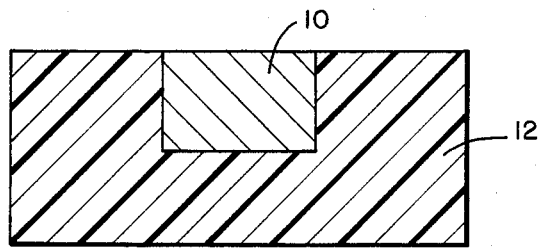
FIG 2 is a sectional view illustrating a sample and its mounting in plastic.

Referring now to the drawings, a sample specimen 10 in accordance with this invention includes an aluminum metal matrix composite material that is filled with silicon carbide. A specific specimen 10 includes for example, 6061 aluminum alloy with 25 volume percent silicon carbide. A method for providing a smooth and flat surface of the specimen is needed in order to adequately determine and examine the shape and size of individual particulate of the aluminum metal matrix in the composite material. In order to properly prepare the surface of sample 10 for appropriate examination, the special method as set forth herein and as illustrated in the flow chart of FIG. 1 has been found to provide an appropriate method for preparing sample surface for proper examination. In accordance with this invention, sample 10 which has been cut from a parent metal material is incapulated in suitable plastic such as a plastic selected from either thermo-setting or epoxy resin material 12 and specimen 10 is mounted in material 12 prior to polishing. With specimen 10 mounted in plastic 12, the metallographic preparation method for surfacing specimen 10 is divided into four stages:

1. Rough Grinding
2. Fine Grinding
3. Rough Polishing
4. Final Polishing

Stage I—Rough Grinding

Sample 10 mounted in holder material 12 is rough ground on a belt surfacer at approximately 1725 rpm using a 120 grit silicon carbide belt with water and water soluable oil as a libricant with sample 10 being ground until the surface is flat and there is no evidence of marks or scratches from previous cutting or other marks on the upper surface of specimen 10. The purpose of this rough grinding stage is to remove most of the disturbed metal resulting from cutting the specimen from the sample material and to obtain a flat surface on specimen 10 prior to the fine grinding stage set forth hereinbelow. Once sample 10 is rough ground the sample is cleaned by running water thereover.

Stage II—Fine Grinding

Fine grinding is accomplished in four steps with a pregrinder and lubricants as described below:

| PAPER | LUBRICANT |
|---|---|
| Step 1 - 220 grit silicon carbide | Water |
| Step 2 - 400 grit silicon carbide | Water |
| Step 3 - 600 grit silicon carbide | Water |
| Step 4 - 1000 grit silicon carbide | Water |

To fine grind sample 10 step 1 is accomplished by moving sample 10 back and forth on the 220 grit silicon carbide paper with water lubricant flowing over the paper with the back and forth grinding taking place on the pregrinder until the 220 grit silicon carbon paper removes scratches and/or deformities on the surfaces of the sample and especially in the direction of the back and forth movement of the sample. Sample 10 is next rotated 90 degrees and moved back and forth on the 400 grit silicon carbide paper with water flowing over the silicon carbide paper until the sample has scratches and/or other deformities removed from the surface of the sample in the direction of the back and forth movement on the silicon paper. With step 2 complete, sample 10 is again rotated an additional 90 degrees in the same direction as previous and moved back and forth on the 600 grit silicon carbide paper with the water lubricant flowing thereover until scratches or other informalities in the surface are removed with the sample being moved back and forth in this particular direction. Finally, sample 10 is rotated an additional 90 degrees to complete the rotation cycle of the sample and moved back and forth on the 1000 grit silicon carbide paper with water lubricant flowing thereover until the scratches and/or informalities of the surface are removed in this back and forth direction also.

The purpose of the rough grinding stages are to obtain the best possible surface that is scratch-free, flat, and relative free of disturbed metal. Sample 10 is cleaned after each fine grinding step with running water thereover before perceeding to the next finer grit as specified in steps 1 through 4.

Polishing—The polishing operation is accomplished by lapping the face of sample 10 on a flat wheel of a diameter of about 8 inches and in which the wheel is cloth-covered and impregnated with the proper polishing media as set forth in the specific polishing steps hereinbelow. Also, the wheel is lubricated with a compatible fluid as set forth hereinbelow.

Stage III—Rough Polishing

Rough Polishing is done on a flat aluminum wheel of about 8 inches in diameter and is covered with a woven nylon polishing cloth charged with three (3) micron diameter bort paste. Lapping oil is also used as a lubricant on the wheel. Sample 10 is then polished for approximately 20 to 30 seconds at a wheel speed of approximately 300–400 rpm. Sample 10 is then cleaned with liquid detergent and running water.

Stage IV—Final Polishing

Step 1. Polishing of sample 10 in this step is done on a flat aluminum wheel of about 8 inches that is covered with a woven nylon polishing cloth charged with one (1) micron diameter bort paste. Also, lapping oil is again used as a lubricant. Sample 10 is then polished at this fine polishing step for approximately 15–25 seconds at a wheel speed of approximately 300–400 rpm. Sample 10 is then cleaned after this polishing step with liquid detergent and running water.

Step 2. Step 2 polishing is done on a flat aluminum wheel of approximately 8 inches and is covered with a microcloth impregnatd with a water slurry of 0.3 micron alumina powder and a liquid detergent. Step 2 polishing of sample 10 is carried out for approximately 10–15 seconds at a wheel speed of 700–800 rpm. Sample 10 after polishing step 2 is again cleaned with liquid detergent and running water.

Step 3. The third and last step in the fine mechanical polishing of sample 10 is accomplished by using a flat aluminum wheel of approximately 8 inches and covered with a microcloth impregnated with a slurry of distilled water and commercial grade magnesium oxide. Sample 10 is polished for approximately 2 to 5 minutes at a wheel speed of approximately 150–250 rpm. After this polishing step, sample 10 is again washed in warm running water, rinsed with alcohol and dried by hot air from a heat gun. Sample 10 is now ready for microscopic examination to determine quality and completeness of the polishing process. Photomicrograph of a sample processed as set forth hereinabove shows fracture area of a tensile specimen at 500 diameters. This method of processing has been found very effective in preparing particulate filled aluminum metal matrix composite material that has been filled with silicon.

I claim:

1. A method for preparing particulate filled aluminum metal matrix composite material for quality determination comprising, mounting a sample of the material that is to be prepared in a plastic material, rough grinding the sample on a belt surfacer that has a grinding surface of silicon carbide with water and water soluable oil as a lubricant thereon and rough grinding the sample until the surface is relatively flat and with relatively large imperfections removed, fine grinding the sample on a pregrinder that has four paper grit sizes with progressively smaller grit of silicon carbide for each step of the fine grinding and with water flowing over the silicon carbide, moving said sample back and forth on the first and coarsest grit silicon carbide paper to remove scratches on the surface of the sample and moving to the second, third and fourth grit papers and moving the sample back and forth thereon with the sample being rotated 90 degrees each time it is moved from the first, second and third grit paper to the next grit paper, running water over the sample after each fine grinding step, rough polishing said sample on a flat aluminum wheel covered with a woven nylon polishing cloth with about three micron diamond bort paste thereon and lapping oil as a lubricant and polishing said sample for about 20–30 seconds at a wheel speed of about 300/400 rpm, cleaning said rough polished sample in liquid detergent and running water, and final polishing of said sample using three final polishing steps in which the first final polishing step uses the coarsest grinding compound with a lubricant on a wheel to polish the sample, polishing the sample in a second polishing step using a grinding compound of a finer material than that used in the first final polishing step and utilizing detergent as a lubricant for the grinding compound with polishing being done on a wheel, and polishing the sample in a third step of final polishing in which the sample is polished on a wheel covered with a microcloth impregnated with a slurry of distilled water and commercial grade magnesium oxide with the polishing in this step being done for about 2 to about 5 minutes at a wheel speed of about 150/250 rpm to produce a sample that is ready for microscopic examination.

2. A method as set forth in claim 1, wherein said rough grinding is carried out by said belt surfacer at a speed of approximately 1725 rpm and said belt surfacer using a silicon carbide grit belt of about 120 grit.

3. A method as set forth in claim 2, wherein said method further comprises in said fine grinding steps of grinding said sample in the first step using 220 grit silicon carbide paper, in the second step using 400 grit silicon carbide paper, in the third step using 600 grit silicon carbide paper, and in the fourth step using 1000 grit silicon carbide paper.

4. A method as set forth in claim 3, wherein said sample is rough polished in said rough polishing stage for about 20–30 seconds at a wheel speed of approximately 300–400 rpm.

5. A method as set forth in claim 4, wherein said method further comprises in said final polishing step 1, utilizing one micron diamond bort paste as said coarser grinding material and using lapping oil as the lubricant and polishing the sample in step 1 for approximately 15–25 seconds at a wheel speed of approximately 300–400 rpm, in said second final polishing step utilizing less coarse grinding material including a water slurry of about 0.3 micron aluminum powder and a liquid detergent and polishing said sample in this step for approximately 10–15 seconds at a wheel speed of about 700–800 rpm, and in the third final polishing step polishing said sample for about 2 to 5 minutes at a wheel speed of approximately 150–250 rpm.

6. A method as set forth in claim 5, wherein the method further includes washing said sample after said third final polishing step in warm running water, then rinsing with alcohol and finally drying by hot air from a heat gun prior to being readied for said microscopic examination.

* * * * *